(12) United States Patent
Wolter

(10) Patent No.: US 9,775,658 B2
(45) Date of Patent: Oct. 3, 2017

(54) BONE PLATE SYSTEM

(71) Applicant: Dietmar Wolter, Hoisdorf (DE)

(72) Inventor: Dietmar Wolter, Hoisdorf (DE)

( * ) Notice: Subject to any disclaimer, the term of this patent is extended or adjusted under 35 U.S.C. 154(b) by 241 days.

(21) Appl. No.: 14/767,233

(22) PCT Filed: Feb. 13, 2014

(86) PCT No.: PCT/EP2014/052787
§ 371 (c)(1),
(2) Date: Aug. 11, 2015

(87) PCT Pub. No.: WO2014/125005
PCT Pub. Date: Aug. 21, 2014

(65) Prior Publication Data
US 2015/0374419 A1 Dec. 31, 2015

(30) Foreign Application Priority Data

Feb. 14, 2013 (EP) ..................................... 13155242

(51) Int. Cl.
*A61B 17/80* (2006.01)
*A61B 17/70* (2006.01)
*A61B 17/86* (2006.01)

(52) U.S. Cl.
CPC ...... *A61B 17/8042* (2013.01); *A61B 17/7059* (2013.01); *A61B 17/8014* (2013.01); *A61B 17/8085* (2013.01); *A61B 17/8605* (2013.01)

(58) Field of Classification Search
CPC ........................ A61B 17/8042; A61B 17/8033
See application file for complete search history.

(56) References Cited

U.S. PATENT DOCUMENTS

| 4,794,918 | A | * | 1/1989 | Wolter ............... A61B 17/8042 606/287 |
| 5,397,363 | A | | 3/1995 | Gelbard |
| 6,406,478 | B1 | | 6/2002 | Kuo |
| 2006/0122605 | A1 | | 6/2006 | Suh et al. |
| 2010/0057134 | A1 | | 3/2010 | Lowry |
| 2011/0118784 | A1 | | 5/2011 | Baynham |

FOREIGN PATENT DOCUMENTS

| EP | 0201024 | 4/1986 |
| EP | 0242842 | 10/1987 |

OTHER PUBLICATIONS

English Translation of IPER.
Search Report.

* cited by examiner

*Primary Examiner* — Andrew Yang
(74) *Attorney, Agent, or Firm* — Alix, Yale & Ristas, LLP

(57) ABSTRACT

The invention relates to a bone plate system with a bone plate, a pressure plate, and a bone screw. The bone plate comprises a through-hole, said through-hole having a seat surface with a variable angle for the bone screw. In the connected state of the system, the bone screw is inserted into the through-hole. The head of the bone screw is enclosed between the bone plate and the pressure plate. The pressure plate is fixed to the bone plate via a screw connection which has two securing screws. The axes of the securing screws spread apart such that the distance between the axes of the securing screws increases in the screw-in direction. The head of the bone screw is thereby reliably fixed between the pressure plate and the bone plate.

20 Claims, 5 Drawing Sheets

BONE PLATE SYSTEM

BACKGROUND

The invention relates to a bone plate system comprising a bone plate, a pressure plate and a bone screw. The bone plate comprises a through-hole having a seat surface with a variable angle for the bone screw. In a connected state of the system, the bone screw is inserted into the through-hole and the head of the bone screw is enclosed between the bone plate and the pressure plate. A screw connection comprising two fastening screws is provided for fastening the pressure plate to the bone plate.

Bone plates of this kind are fixed to the bone by guiding the bone screw through the through-hole and screwing it into the bone substance. The bone plates are used, for example, to fix bones or bone fragments relative to each other. Other uses are also possible, for example ones in which the bone plate is an element of a prosthesis, such as a joint prosthesis.

Since the seat surface of the through-hole is designed such that it can receive the bone screw at different angles, the surgeon is able, during the operation, to freely choose, within certain limits, the angle at which he screws in the bone screw. He is thus able to insert the bone screw in the way that best corresponds to the anatomical conditions.

The pressure plate is then connected to the bone plate such that the head of the bone screw is clamped between the pressure plate and the bone plate. The bone screw is thus fixed at the selected angle relative to the bone plate. The angle stability between the bone screw and the bone plate has the effect that less load is transmitted between the bone screw and the bone substance per unit of surface area, as a result of which the bone substance is preserved. A bone plate system of this kind is known from EP 0 201 024 A1, for example.

SUMMARY

A bone plate system in which the bone screw is able to be fixed with a high degree of reliability is proposed. The axes of the fastening screws are spread apart such that the distance between the axes of the fastening screws increases in the screwing-in direction.

The spreading apart of the axes has the effect that the pressure plate, in the connected state, is subject to a tensile stress that acts in a direction parallel to the plane of the bone plate. By means of this tensioning, the bone screw is given additional hold. The bone screw is thus fixed relative to the bone plate with increased reliability.

The bone plate system can be designed such that the pressure plate is held at a distance from the bone plate, by the head of the bone screw inserted into the bone plate, when the pressure plate is in an untensioned state. This means that the untensioned pressure plate cannot bear flat on the bone plate when the head of the bone screw is enclosed between the bone plate and the pressure plate.

To produce the screw connection between the pressure plate and the bone plate, the fastening screws are each guided through a receiving opening of the pressure plate and inserted into a bore of the bone plate. To ensure that the fastening screws can easily be brought into engagement, it is advantageous if a first receiving hole of the pressure plate is flush with a first bore of the bone plate and a second receiving hole of the pressure plate is flush with a second bore of the bone plate when the pressure plate is untensioned. This is preferably the case when the untensioned pressure plate is at a distance from the bone plate. The pressure plate can then be placed onto the head of the bone screw, and both fastening screws can be brought into engagement without tensioning.

The pressure plate is subjected to tensioning only when the fastening screws are tightened. On the one hand, this has the effect that the ends of the pressure plate are drawn closer to the bone plate, such that the pressure plate is deformed in an arc shape, i.e. is under a bending stress, in the assembled state of the bone plate system. On the other hand, the pressure plate is tensioned in an outward direction, such that the pressure plate is under tensile stress in the assembled state of the bone plate system. Both effects contribute to fixing the head of the bone screw securely between the pressure plate and the bone plate.

With the bending of the pressure plate, the angle in relation to the fastening screw changes. Since stresses between the head of the fastening screw and the pressure plate are undesirable, it is advantageous if a receiving seat of variable angle is provided between the head of the fastening screw. The first receiving hole and/or the second receiving hole of the pressure plate can therefore have a seat surface with a variable angle for the fastening screw. For example, the seat surface can be shaped spherically, and the head of the fastening screw can have a shape adapted thereto.

The angle enclosed by the axes of the fastening screws can be, for example, between 5° and 30°, preferably between 10° and 20°. Tests have shown that good results are also achieved with a greater angle. For example, the angle can also lie between 30° and 90°.

The bores provided in the bone plate and intended for the fastening screws can be designed as blind bores or as continuous bores. The bore can have an inner thread, into which the fastening screw can be screwed. Preferably, the bores enclose between themselves one or more of the through-holes intended for the bone screws. The axis of the bore preferably encloses, with a tangential plane joining the bone plate in the area of the bore, an angle that is not equal to 90°. For example, the angle can lie between 40° and 85°.

The pressure plate can have a manipulation opening such that, in the connected state, the head of the bone screw is accessible through the manipulation opening. By means of such a manipulation opening, it is possible to connect the pressure plate to the bone plate even before the bone screw is brought to its final position relative to the bone plate. Even after the placement of the pressure plate, the bone screw can be accessed through the manipulation opening, for example in order to change the position of the bone part connected to the bone screw. When the bone screw has taken up its final position relative to the bone plate, the pressure plate can be tensioned against the bone plate such that the head of the bone screw is fixed between the pressure plate and the bone plate.

The through-hole has, in one direction, a diameter that is smaller than the diameter of the screw head, such that the screw head is received by the seat surface of the through-hole. Preferably, the seat surface is designed such that the screw head has, in the direction in question, a defined position relative to the bone plate. The through-hole can be designed such that the bone screw can also not be moved relative to the bone plate in other directions. The position of the screw head in the bone plate is then unambiguously defined, and it is only the orientation of the shank that can be varied.

It is also possible that the through-hole has, in one direction, a diameter that is greater than the diameter of the screw head. In this direction, the bone plate can be moved relative to the bone screw. This can be made use of, for example, in order to bring the relevant bone parts into the correct position relative to each other after the bone screw has been screwed in.

If the through-hole has, in one direction, a greater diameter than the screw head, the seat surface can be designed in the manner of a rail along which the screw head can be moved continuously and can adopt any desired intermediate positions. In other embodiments, the seat surface can be provided with projections which define a plurality of preferred positions for the screw head.

The manipulation opening is preferably likewise designed such that it has, in one direction, a diameter that is smaller than the diameter of the screw head. The areas of the pressure plate that adjoin the manipulation opening can then exert pressure on the screw head in order to fix the bone screw in the desired position. This direction preferably coincides with the direction in which the through-hole has its smallest diameter when the pressure plate is connected to the bone plate.

In another direction, the manipulation opening can have a diameter that is greater than the diameter of the screw head. The screw head can then be accessed through the manipulation opening in order to move the bone screw relative to the bone plate. The manipulation opening can likewise be designed in the manner of a rail, along which the screw head can be moved continuously. Alternatively, the manipulation opening can be provided with projections which define a plurality of preferred positions for the bone screw.

The smallest diameter of the manipulation opening should be greater than the diameter of the tool with which the bone screw is maneuvered. The tool can then be guided through the manipulation opening in order to engage in the screw head. If the bone screw has, in the screw head, a socket (for example in the form of a hexagon profile) which is designed for the engagement of a tool, the diameter of the manipulation opening is preferably greater than the diameter of the socket.

In the connected state, the pressure plate is connected to the bone plate, such that the head of the bone screw is enclosed between the pressure plate and the bone plate. The connection is such that the pressure plate can be tensioned against the head of the bone screw. Although the head of the bone screw is already enclosed between the bone plate and the pressure plate before the pressure plate is clamped, the bone screw can still be moved relative to the bone plate and the pressure plate.

The two fastening screws of the screw connection between the pressure plate and the bone plate can be arranged such that they enclose the manipulation opening between themselves.

To ensure that the pressure plate can give the screw head a secure hold, measures can be provided by which the friction between the screw head and the pressure plate is increased. For example, the screw head can be provided with surface structuring in the area of contact in which the pressure plate bears on the screw head. The surface structuring can extend around the socket of the screw head into which the tool is inserted. For example, a plurality of projections can be formed from this edge and narrow to a point in the axial direction of the bone screw.

The hold can be further improved if the pressure plate is made of a softer material than the bone screw. The pressure plate is then able to deform under the pressure of the screw head, such that there is improved engagement between the screw head and the pressure plate. If the structuring on the head of the bone screw engages in the material of the pressure plate, it is even possible to obtain a form-fit connection. The bone screw can be made, for example, of a titanium alloy such as TiAl6V4. The pressure plate can be made of pure titanium, preferably grade 0, grade 1, grade 2 or grade 3.

If the pressure plate is made of a softer material than the bone plate, this is advantageous for being able to tension the pressure plate with the fastening screws. The pressure plate then has increased elasticity and can be subjected to a bending stress and a tensile stress, without the bone plate being exposed to great forces. Particularly if the elasticity of the pressure plate is increased in this way, the fastening screw can also enclose a greater angle with a tangential plane that joins the bone plate in the area of the bore. For example, the angle can lie between 5° and 60°, preferably between 30° and 50°.

The pressure plate can be made entirely of the softer material. Alternatively, it is also possible that the pressure plate comprises a pressure plate body and an inlay, wherein only the inlay is made of the softer material. Preferably, the inlay forms the contact area with which the pressure plate bears on the screw head. By means of the pressure plate body, the pressure plate acquires greater stability than it has if it is made entirely of the softer material. As has been described the inlay can be made of pure titanium. The pressure plate body can be made of the titanium alloy TiAl4V6, for example.

In a preferred embodiment, the bone plate system comprises more than one pressure plate according to the invention, wherein each pressure plate is assigned to a through-hole of the bone plate. The bone plate can have one or more further through-holes to which no pressure plate is assigned.

For the angle variability between the bone screw and the bone plate, it is advantageous if the surface of the screw head bearing on the seat surface of the through-hole has an approximately hemispherical shape. Seen in cross section, the seat surface of the through-hole preferably has a hemispherical shape matching this. In the context of the invention, it is advantageous if the angle between the bone screw and the bone plate can be varied continuously, i.e. it is not merely possible to choose between a plurality of predefined directions.

BRIEF DESCRIPTION OF THE DRAWINGS

The invention is described below with reference to advantageous illustrative embodiments depicted in the attached drawings, in which.

DETAILED DESCRIPTION

Figure 1:
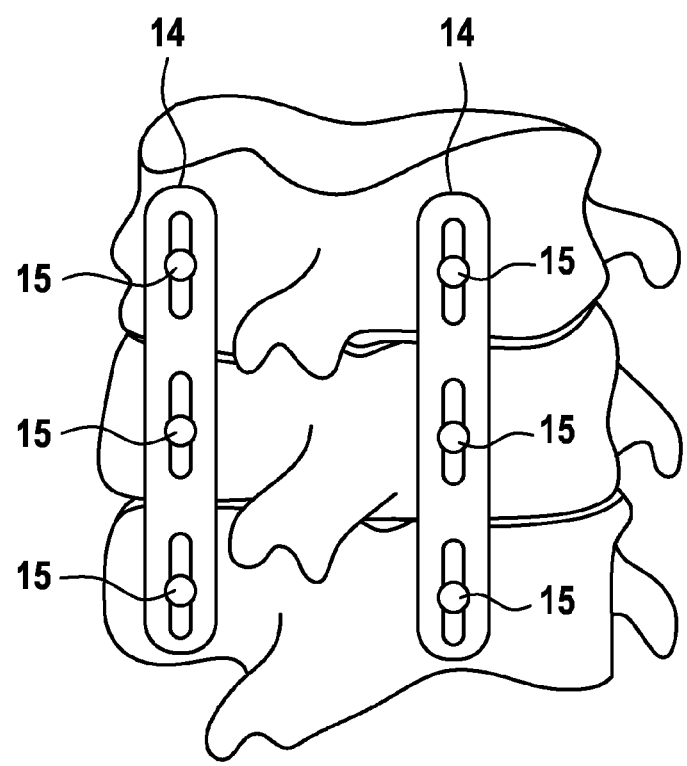
FIG. 1 shows a schematic view of an example of use of a bone plate system.

FIG. 1 is an oblique dorsal view of a portion of a human spinal column, specifically a portion comprising three vertebral bodies. The middle vertebral body has sustained a fracture as a result of an accident. Using two bone plates 14, the upper vertebral body and the lower vertebral body are fixed relative to each other such that the load on the middle vertebral body is removed and the latter is able to heal at rest. The bone plate 14 is fastened to the vertebral bodies by bone screws 15, which are screwed into the pedicles of the vertebral body. The patient lies in the prone position during the operation. The surgeon creates an access to the vertebral bodies from the back. This type of dorsal fixation goes back to Roy Camille.

Figure 2:
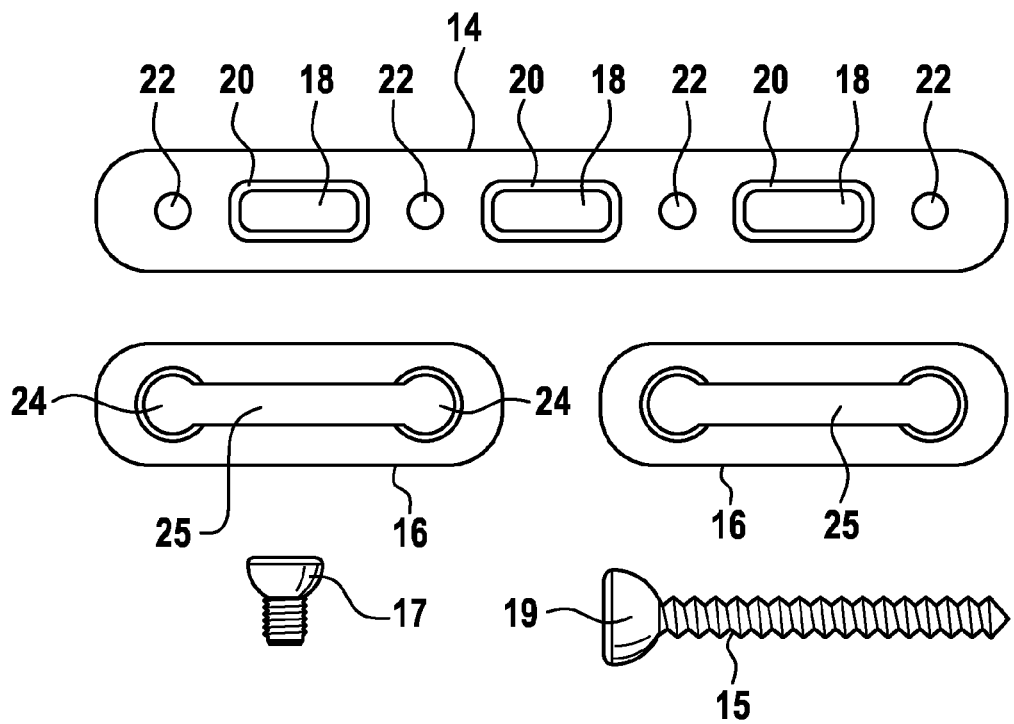
FIG. 2 shows the components of a bone plate system.

According to FIG. 2, the bone plate system comprises a bone plate 14, two pressure plates 16, and a plurality of bone screws 15 and fastening screws 17.

Figure 5:
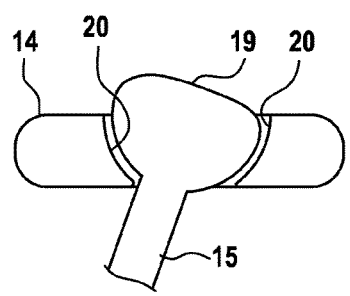
FIG. 5 shows a cross-sectional view of a bone plate system in the connected state.

The bone plate 14 has three through-holes 18, of which the diameter in the transverse direction of the bone plate 14 corresponds to the diameter of the head 19 of the bone screw 15. Each through-hole 18 is provided with a seat surface 20 which, according to FIG. 5, has the shape of a segment of a circle in cross section, such that the hemispherical head 19 of the bone screw 15 bears flat on the seat surface 20 in different orientations of the bone screw 15. The seat surface 20 can therefore receive the bone screw 15 at variable angles. In the transverse direction of the bone plate 14, the position of the bone screw 15 is clearly defined within the through-hole 18. In the longitudinal direction of the bone plate 14, the bone screw 15 can be moved within the through-hole 18.

Figure 3:
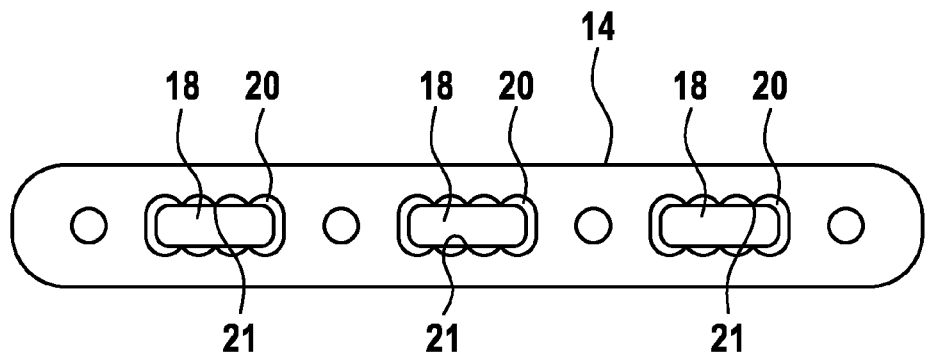
FIG. 3 shows an alternative embodiment of a bone plate.

In the embodiment shown in FIG. 2, the seat surfaces 20 of the through-holes 18 are designed in the longitudinal direction in the manner of a rail, along which the bone screws 15 can be moved continuously and can lie in any desired intermediate positions. In the alternative embodiment of FIG. 3, projections 21 are formed in the seat surface 20 and define specific preferred positions for the head 19 of the bone screw 15. The head 19 of the bone screw 15 then bears fully on the seat surface 20 when it is positioned between two projections 21.

Figure 4:
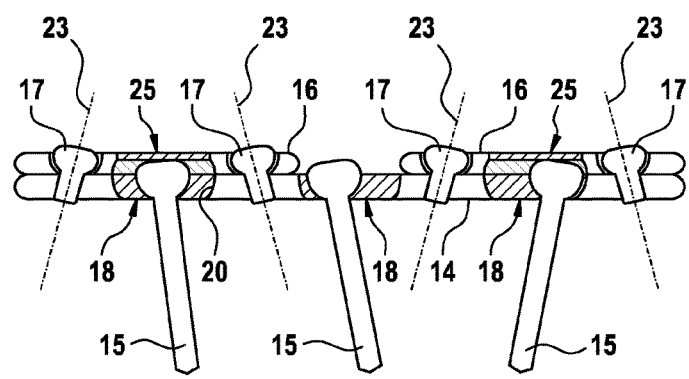
FIG. 4 shows a schematic sectional view of a bone plate system.

The bone plate 14 moreover comprises four bores 22. The bores 22 are provided with an inner thread, which matches the thread of the fastening screws 17. The bores 22 are not oriented at right angles to the plane of the bone plate 14, and instead the axes 23 of the bores 22 are inclined according to FIG. 4. The two outer through-holes 18 of the bone plate 14 are each enclosed between two bores 22. In relation to the enclosed through-hole 18, the axes 23 of the bores 23 are spread apart, and therefore the distance between the axes 23 increases in the screwing-in direction.

The pressure plates 16 of the bone plate system each have two openings 24, the distance between the latter being adapted to the distance between the bores 22 in the bone plate 14. When the pressure plate 16 is placed onto the bone screw 15, the fastening screws 17 can be guided through the openings 24, and the fastening screws 17 are screwed into the bores 22. In this way, the pressure plate 16 is tensioned and pressed against the bone plate 14. On account of the spreading apart of the bores 22, the pressure plate 16 is exposed to a bending stress and to a tensile stress in the longitudinal direction of the bone plate 14.

Figure 6:
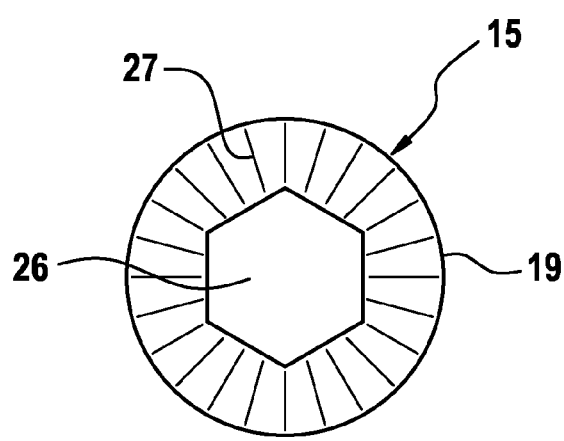
FIG. 6 shows a plan view of the head of a bone screw.

A manipulation opening 25 extends between the two openings 24 that are provided for the fastening screws 17, wherein the manipulation opening 25 in the present illustrative embodiment produces an uninterrupted connection between the two openings 24. Viewed in the transverse direction, the diameter of the manipulation opening 25 is slightly greater than the diameter of the hexagonal socket 26 shown in the head 19 of the bone screw 15 in FIG. 6. A screwdriver fitting the socket 26 can therefore be guided through the manipulation opening 25.

When the bone plate system is used in the context of the operation shown in FIG. 1, the bone plate 14 is placed onto the vertebral bodies, and the bone screws 15 are screwed into bores of the vertebral body. In the first step, the bone screw 15 is screwed in to the extent that the head 19 of the bone screw 15 reaches the area of the through-hole 18. However, the bone screw 15 is not yet tightened so much that that it tensions the bone plate 14 against the vertebral body.

The pressure plate 16 is then placed onto the bone plate 14 such that the head 19 of the bone screw 15 is enclosed between the pressure plate 16 and the bone plate 14. With the fastening screws 17, the pressure plate 16 is fastened to the bone plate 14. In the first step, the fastening screws 17 are also not yet tightened to the extent that the head 19 of the bone screw 15 is clamped. The bone plate system is then in a state in which the bone screw 15 can still be moved relative to the through-hole 18.

A screwdriver can now reach through the manipulation opening 25 into the hexagonal socket 26 of the bone screw 15. If a screwdriver is inserted into each of the two bone screws 15 arranged at the outside, the screwdrivers can be engaged by expansion forceps, such that the outer vertebral bodies are spread apart from each other and the load on the middle vertebral body is removed. Moreover, the angle between the bone screw and the bone plate can be changed in order to orient the vertebral bodies correctly to each other.

When the vertebral bodies have in this way been brought to the desired position, the bone screws can be tightened with the screwdriver, such that the bone plate is tensioned against the vertebral bodies. The fastening screws are then tightened, such that the head of the bone screw is clamped between the pressure plate and the bone plate. The bone screw is then connected to the bone plate at a stable angle, as a result of which the connection between the bone screw and the vertebral body is relieved. The bone substance is therefore exposed to less loading than would be the case if the bone screw were movable relative to the bone plate.

The pressure plate 16 is made of pure titanium grade 1 and is therefore softer than the bone screw, which is made of TiAl6V4. The material of the pressure plate 16 deforms when the pressure plate is tensioned against the head 19 of the bone screw 15. In the contact area in which the pressure plate 16 bears on the bone screw 15, the head of the bone screw 15 provided with a surface structure 27 comprising a multiplicity of radially oriented elevations and depressions. The elevations can penetrate into the material of the pressure plate 16, such that a form-fit connection is established between the surface structure 27 and the pressure plate 16.

Figure 7:
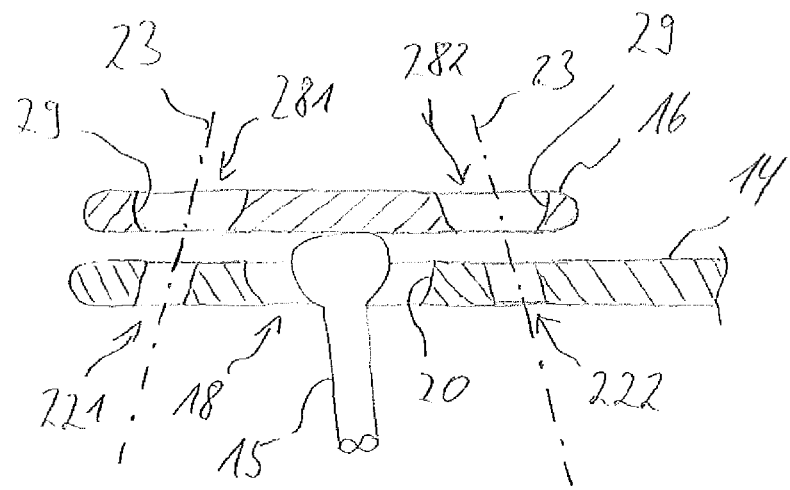
FIG. 7 shows an alternative embodiment of a bone plate system.
Figure 8:
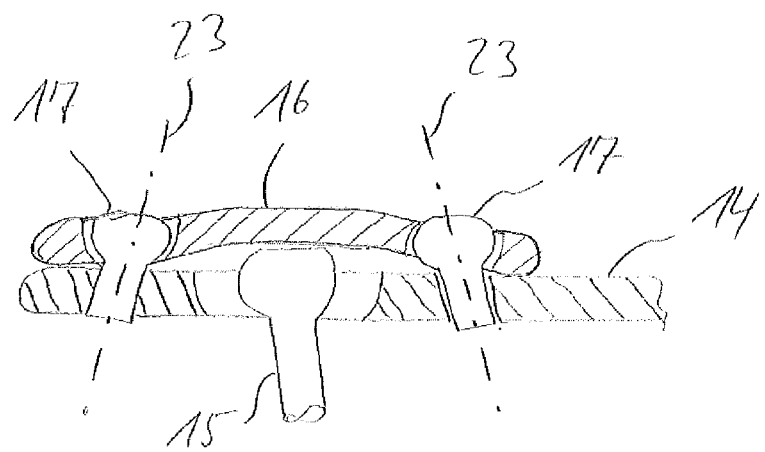
FIG. 8 shows the bone plate system from FIG. 7 in the assembled state.

In the alternative embodiment of FIGS. 7 and 8, the pressure plate 16 has no manipulation opening. In this illustrative embodiment, the bone screw 15 is first of all tightened to its final position before the pressure plate 16 is connected to the bone plate 14. In this state, the bone screw 15 protrudes above the surface of the bone plate 14, such that the pressure plate 16, which is placed onto the bone screw 15, is at a distance from the bone plate 14. This state, in which the pressure plate 16 is placed onto the bone screw 15 but is not yet connected to the bone plate 14, is shown in FIG. 7.

The axis 23, along which the fastening screw 17 is brought into engagement with the inner thread of the bore 221, 222, extends centrally through the receiving opening 281, 282 of the pressure plate 16. Since both receiving openings 281, 282 are flush with a respective bore 221, 222, the screw connection between the pressure plate 16 and the bone plate 14 can be produced easily, without one of the elements being tensioned. If the pressure plate 16 were to bear flat on the bone plate 14, the receiving openings 281, 282 would not be flush with the bores 221, 222.

The tensioning arises only when the fastening screws 17 are tightened such that the outer ends of the pressure plate 16 are drawn against the bone plate 14. The pressure plate 16 is thus subjected both to a bending stress and also to a tensile stress in the longitudinal direction. This has the effect that the bone screw 15 is reliably fixed.

The angle between the head of the fastening screw 17 and the receiving opening 28 changes during tightening. The seat surface 29 of the receiving opening 28 has a spherical shape, such that the hemispherical underside of the head of the fastening screw 17 can slide on the seat surface 29. Unnecessary stresses between the fastening screw 17 and the pressure plate 16 are thereby avoided.

The invention claimed is:

1. A bone plate system, comprising a bone plate with a through-hole, a pressure plate, and a bone screw, wherein the through-hole has a seat surface with a variable angle for the bone screw, and wherein, in a connected state of the system, the bone screw is inserted into the through-hole and a head of the bone screw is enclosed between the bone plate and the pressure plate, wherein a screw connection comprising two fastening screws is provided for fastening the pressure plate to the bone plate in a screwing-in direction, characterized in that the fastening screws have axes separated by a distance and the axes of the fastening screws are spread apart such that the distance between the axes of the fastening screws increases in the screwing-in direction.

2. The bone plate system as claimed in claim 1, characterized in that the pressure plate has a first receiving hole and a second receiving hole for the fastening screws, in that the bone plate has a first bore and a second bore for the fastening screws, wherein the first receiving hole is flush with the first bore and the second receiving hole is flush with the second bore when the pressure plate is at a distance from the bone plate.

3. The bone plate system as claimed in claim 2, characterized in that the first receiving hole and/or the second receiving hole has a seat surface with a variable angle for the fastening screw.

4. The bone plate system as claimed in claim 2, characterized in that the pressure plate has a manipulation opening such that, in the connected state, the head of the bone screw is accessible through the manipulation opening.

5. The bone plate system as claimed in claim 2, characterized in that the head of the bone screw has a diameter and the through-hole has, in one direction, a diameter that is greater than the diameter of the head of the bone screw.

6. The bone plate system as claimed in claim 1, characterized in that the first receiving hole and/or the second receiving hole has a seat surface with a variable angle for the fastening screw.

7. The bone plate system as claimed in claim 6, characterized in that the pressure plate has a manipulation opening such that, in the connected state, the head of the bone screw is accessible through the manipulation opening.

8. The bone plate system as claimed in claim 6, characterized in that the head of the bone screw has a diameter and the through-hole has, in one direction, a diameter that is greater than the diameter of the head of the bone screw.

9. The bone plate system as claimed in claim 1, characterized in that the pressure plate has a manipulation opening such that, in the connected state, the head of the bone screw is accessible through the manipulation opening.

10. The bone plate system as claimed in claim 9, characterized in that the receiving holes are arranged such that they enclose the manipulation opening therebetween.

11. The bone plate system as claimed in claim 9, characterized in that the manipulation opening has a smallest diameter and a tool for the bone screw has a diameter and the smallest diameter of the manipulation opening is greater than the diameter of a tool provided for the bone screw.

12. The bone plate system as claimed in claim 1, characterized in that the head of the bone screw has a diameter and the through-hole has, in one direction, a diameter that is greater than the diameter of the head of the bone screw.

13. The bone plate system as claimed in claim 12, characterized in that the seat surface of the through-hole is configured like a rail.

14. The bone plate system as claimed in claim 12, characterized in that the seat surface of the through-hole is provided with projections, and in that the projections define a plurality of preferred positions for the head of the bone screw.

15. The bone plate system as claimed in claim 1, characterized in that the head of the bone screw has a diameter and the manipulation opening has, in one direction, a diameter that is greater than the diameter of the head of the bone screw.

16. The bone plate system as claimed in claim 1, characterized in that the head of the bone screw is provided with surface structuring in an area of contact with the pressure plate.

17. The bone plate system as claimed in claim 1, characterized in that the pressure plate has a material and the bone screw has a material and the material of the pressure plate is softer than the material of the bone screw.

18. The bone plate system as claimed in claim 17, characterized in that the pressure plate is made of pure titanium.

19. The bone plate system as claimed in claim 18, characterized in that the pressure plate is made of pure titanium grade 0, pure titanium grade 1, pure titanium grade 2 or pure titanium grade 3.

20. The bone plate system as claimed in claim 1, characterized in that the pressure plate comprises a pressure plate body and an inlay, wherein the inlay is made of a softer material than the pressure plate body.

* * * * *